United States Patent
Wu et al.

(10) Patent No.: US 9,408,915 B2
(45) Date of Patent: Aug. 9, 2016

(54) TOLVAPTAN SOLID DISPERSION AND ITS PREPARATION METHOD

(75) Inventors: Yuxia Wu, Jiangsu (CN); Shujun Mao, Jiangsu (CN); Hao Chen, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 95 days.

(21) Appl. No.: 13/806,173

(22) PCT Filed: Jun. 2, 2011

(86) PCT No.: PCT/CN2011/075131
§ 371 (c)(1),
(2), (4) Date: Dec. 21, 2012

(87) PCT Pub. No.: WO2011/160541
PCT Pub. Date: Dec. 29, 2011

(65) Prior Publication Data
US 2013/0102588 A1    Apr. 25, 2013

(30) Foreign Application Priority Data
Jun. 25, 2010  (CN) .......................... 2010 1 0224884

(51) Int. Cl.
| A61K 47/32 | (2006.01) |
| A61K 9/10 | (2006.01) |
| A61K 31/55 | (2006.01) |
| A61K 9/14 | (2006.01) |
| A61K 9/20 | (2006.01) |
| A61K 9/16 | (2006.01) |

(52) U.S. Cl.
CPC . *A61K 47/32* (2013.01); *A61K 9/10* (2013.01); *A61K 9/146* (2013.01); *A61K 9/1623* (2013.01); *A61K 9/2018* (2013.01); *A61K 31/55* (2013.01); *A61K 9/1652* (2013.01); *A61K 9/2054* (2013.01); *A61K 9/2077* (2013.01)

(58) Field of Classification Search
None
See application file for complete search history.

(56) References Cited

U.S. PATENT DOCUMENTS

| 2006/0051422 A1* | 3/2006 | Colombo et al. ............. 424/486 |
| 2007/0218012 A1* | 9/2007 | Bittorf et al. .................... 424/45 |
| 2008/0221047 A1* | 9/2008 | Yoshida et al. ................ 514/29 |
| 2010/0233265 A1* | 9/2010 | Suzuki .......................... 424/487 |

FOREIGN PATENT DOCUMENTS

| JP | 11-021241 A | 1/1999 |
| WO | 2008156217 A2 | 12/2008 |

OTHER PUBLICATIONS

Tiwari et al., "Solid Dispersions: An Overview to Modify Bioavailability of Poorly Water Soluble Drugs", 2009, vol. 1, No. 4, pp. 1338-1349.*
Kumar et al., "Enhancement of Solubility and Dissolution Rate of Irbesartan by Solid Dispersion Technique", 2011, Asian Journal of Pharmaceutical and Clinical Research, vol. 4, Issue 2, pp. 36-40.*
JP 1999-21241 English Translation.*
Int'l Search Report issued Sep. 8, 2011 in Int'l Application No. PCT/CN2011/075131.

* cited by examiner

*Primary Examiner* — Robert A Wax
*Assistant Examiner* — Randeep Singh
(74) *Attorney, Agent, or Firm* — Panitch Schwarze Belisario & Nadel LLP

(57) ABSTRACT

A tolvaptan solid dispersion and its preparation method are disclosed. The solid dispersion comprises tolvaptan and cross-linked polyvinylprrolidone at a weight ratio of 1:0.05-20, preferably 1:0.1-10, and more preferably 2:1. The solid dispersion can further comprise one or more water-soluble polymers, such as polyvinylprrolidone, hydroxypropyl cellulose, hydroxyethyl cellulose or methylcellulose, wherein the weight ratio of tolvaptan:the crosslinked polyvinylprrolidone:the water-soluble polymers is preferably 2:1:0.1. The solid dispersion exhibits good thermodynamic stability and solubility. The pharmaceutical composition thereof has improved release rate and bioavailability.

8 Claims, 3 Drawing Sheets

TOLVAPTAN SOLID DISPERSION AND ITS PREPARATION METHOD

CROSS-REFERENCE TO RELATED APPLICATIONS

This application is a Section 371 of International Application No. PCT/CN2011/075131, filed on Jun. 2, 2011, which was published in the Chinese language on Dec. 29, 2011, under International Publication No. WO 2011/160541 A1, and the disclosure of which is incorporated herein by reference.

FIELD OF THE INVENTION

The present invention relates to the field of chemical pharmaceuticals. It discloses a tolvaptan solid dispersion comprising cross-linked polyvinylpyrrolidone.

BACKGROUND OF THE INVENTION

Tolvaptan, 7-chloro-5-hydroxy-1-[2-methyl-4-(2-methylbenzoyl amino)benzoyl]-2,3,4,5,-tetrohydro-1H-benzoazepine represented by the following general formula is used as a vasopressin antagonist.

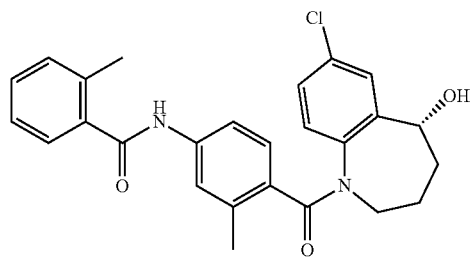

The U.S. Food and Drug Administration has approved the new drug application of tolvaptan (vasopressin receptor 2 antagonist) manufactured by Otsuka Pharmaceutical Co. In a heart failure model, tolvaptan only exhibited hydragogue diuresis effected and decreased heart preload significantly, while having no effect on heart afterload and renal failure. Many clinical trials for treating heart failure and hyponatremia have proven that tolvaptan can decrease fluid retention and increase the serum sodium concentration. Tolvaptan can also relieve the symptom of pulmonary congestion, cause weight loss, protect the kidney function and has no severe adverse effects. It has been proven that tolvaptan is specifically useful in the treatment of clinically significant hypervolemic and normovolemic hyponatremia associated with congestive heart failure, cirrhosis and the syndrome of inappropriate antidiuretic hormone (SIADH).

Tolvaptan, white crystal or crystalline powder, is only slightly soluble in water. Therefore it is inevitable for tolvaptan to have a low bioavailability when administered orally.

In order to solve this problem, Japanese Patent No. JP 11021241 A disclosed a preparation method of a solid tolvaptan composition comprising the following steps: tolvaptan and hydroxypropyl cellulose are dissolved in an organic solvent at a certain ratio, the organic solvent is removed via spray dry method to obtain tolvaptan solid dispersion composition, and other pharmaceutically acceptable excipients are added to obtain the final solid preparation.

DESCRIPTION OF THE INVENTION

The inventors unexpectedly discovered that a tolvaptan solid dispersion made of tolvaptan and a carrier comprising cross-linked polyvinylpyrrolidone showed superior solubility and stability of the active ingredient compared to the preparation containing hydroxypropyl cellulose known in the prior art. Moreover, it is more convenient to formulate it into conventional solid dosage forms. The inventors also discovered that adding one or more other water soluble polymers in addition to the cross-linked polyvinylpyrrolidone can further improve the dissolution rate.

An object of the present invention is to provide a novel tolvaptan solid dispersion which exhibits improved solubility and bioavailability compared to the traditional preparation, and the preparation method thereof.

Another object of the present invention is to provide a pharmaceutical composition for oral administration, which comprises tolvaptan solid dispersion.

In one embodiment of the present invention, a solid dispersion comprising amorphous tolvaptan or a salt of amorphous tolvaptan as the active ingredient and cross-linked polyvinylpyrrolidone is provided. The ratio, by weight, of tolvaptan or the salt of tolvaptan and the cross-linked polyvinylpyrrolidone is in the range of 1:0.05~20, preferably 1:0.1~10, and more preferably 2:1.

The present solid dispersion can consist only of the active ingredient and the cross-linked polyvinylpyrrolidone. Furthermore, one or more water soluble polymers can be added to the present solid dispersion to improve the physical properties of the present dispersion. The water soluble polymers can be the common soluble polymers used in the art which include, but are not limited to, alkyl cellulose, such as methyl cellulose; hydroxyalkyl cellulose, such as hydroxymethyl cellulose, hydroxyethyl cellulose, hydroxypropyl cellulose, and hydroxybutyl cellulose; hydroxyalkylalkyl cellulose, such as hydroxyethylmethyl cellulose, hydroxypropylmethyl cellulose; carboxyalkyl cellulose, such as carmellose; alkali metal salts of carboxyalkyl cellulose, such as sodium carboxymethyl cellulose; carboxyalkylalkyl cellulose, such as carboxymethylethyl cellulose; carboxyalkyl cellulose esters; pectin, such as sodium carboxymethyl amylopectin; chitin derivatives, such as chitosan; polysaccharide, such as alginic acid and the alkali metal salts or ammonium salts thereof, carrageenans, galactomannans, tragacanth gum, agar, acacia, guar gum, and xanthum gum; polymethacrylic acid and the salts thereof; polymethacrylic acid and the salts thereof, methacrylate copolymer, aminoalkyl methacrylate copolymer; polyvinyl acetal and diethylamino acetate; sugar surfactant, such as sucrose distearate, sucrase mono/distearate, sucrose monopalmitate; polyvinyl alcohol; polyvinylpyrrolidone and polyvinylpyrrolidone-vinyl acetate copolymer; polyalkylene oxide, such as polyethylene oxide and polypropylene oxide; and ethylene oxide-propylene oxide copolymers.

Of the above water soluble polymers, alkyl cellulose, hydroxyalkyl cellulose, carboxyalkylalkyl cellulose or the alkali metal salts thereof, and polyvinylpyrrolidone are preferable, hydroxypropylmethyl cellulose and cross-linked polyvinylpyrrolidone are more preferable. In a preferred embodiment, the ratio, by weight, of the water soluble polymers and the cross-linked polyvinylpyrrolidone is in the range of 1:5~20, more preferably 1:8~15, and most preferably 1:10.

It is shown that because water soluble polymers can improve the properties of solid dispersions, there is no particular limitation on the amount of the water soluble polymers to be added. A person skilled in the art can choose the amount according to the practical production. It is shown in the research that when the ratio, by weight, of the water soluble polymers and the cross-linked polyvinylpyrrolidone reaches 1:5~20, more preferably 1:8~15, and most preferably 1:10, the preparation shows a significantly improved effect.

Moreover, compositions are described in the examples of the present application, which illustrate the improved effect according to preferred embodiments of the present invention. A preferred embodiment of the present invention comprises a solid dispersion having the following components and ratio:

| Component | Weight ratio |
|---|---|
| Tolvaptan | 2 |
| Cross-linked polyvinylpyrrolidone | 1 |
| Water-soluble polymer(s) | 0.1 | wherein the water soluble polymer(s) comprises one or more of polyvinylpyrrolidone, hydroxypropyl cellulose, hydroxyethyl cellulose or methyl cellulose, preferably polyvinylpyrrolidone and hydroxypropyl cellulose.

When water soluble polymers are contained in the composition, the solid dispersion can consist only of the active ingredient, the cross-linked polyvinylpyrrolidone and the water soluble polymer(s), without any other components.

In the preparation of an amorphous tolvaptan solid dispersion according to embodiments of the present invention, the cross-linked polyvinylpyrrolidone can be used alone or in combination with the water soluble polymer(s) as the carrier. A practical preparation comprises the following steps:

(1) dissolving tolvaptan or a salt of tolvaptan in an organic solvent;
(2) when the solid dispersion carrier does not comprise a water soluble polymer, dissolving or dispersing cross-linked polyvinylpyrrolidone in an organic solvent;
when the solid dispersion carrier comprises a water soluble polymer, dissolving or dispersing cross-linked polyvinylpyrrolidone and the water soluble polymer in one organic solvent at the same time to obtain a solution, or dissolving or dispersing cross-linked polyvinylpyrrolidone and the water soluble polymer in two organic solvents to obtain two solutions, wherein the organic solvents can comprise water according to the need for dissolving or dispersing the drug or the solid dispersion carrier; and
(3) mixing the above solutions of the drug and the solid dispersion carrier, and removing the organic solvents, to thereby obtain the solid dispersion composition.

To obtain the solid dispersion preparation, the organic solvent can be removed by conventional methods in the art, such as evaporation, a spray drying process or a fluidized bed drying process. For the present invention, the spray drying process is preferred.

Any organic solvent that can easily dissolve or disperse the drug and the solid dispersion carrier above can be used. Examples of the organic solvent include low alcohols such as methanol, ethanol, and isopropanol; ketones such as acetone and butanone; halogenated hydrocarbons such as dichloromethane, dichloroethane, trichloromethane, and carbon tetrachloride; and the mixtures thereof. At the same time, water can be added if necessary. Among them, the mixture of small alcohols and halogenated hydrocarbons such as methanol, ethanol, isopropanol, acetone, butanone, dichloromethane, dichloroethane, trichloromethane, or carbon tetrachloride are particularly preferred in terms of solubility and distillation. The mixture of dichloromethane and methanol or ethanol is particularly preferred. In a preferred embodiment, the mixture of ethanol and dichloromethane is used to dissolve tolvaptan or its salt, and the mixture of ethanol and dichloromethane is used to dissolve cross-linked polyvinylpyrrolidone and water soluble polymers.

The range of the particle diameters of the amorphous solid dispersion of the present invention is in the range of 0.01~400 μm, preferably 0.1~300 μm, and more preferably 1~200 μm.

The tolvaptan solid dispersion of the present invention shows no endothermic peak in the differential scanning calorimetry (DSC) curve and no crystallization refraction peak in the X-ray powder diffraction pattern, which proves that the tolvaptan included in the present dispersion is stable in amorphous form.

Moreover, the present invention provides a pharmaceutical composition comprising the solid dispersion of the present invention and a pharmaceutically acceptable carrier, excipient, or additive known in the art for oral administration. The pharmaceutical composition can be prepared into conventional dosage forms, such as powders, granules, tablets, soft or hard capsules, pills or coated forms. For example, the solid dispersion in the form of powder or granules can be put into the hard capsule with lubricants or other pharmaceutical additives, or it can be pressed into tablets, the tablets then coated with the pharmaceutical additives using conventional methods to obtain coating forms.

The present preparation can be administered orally in a single dose or separate doses.

In the present invention, one or more pharmaceutical excipients can optionally be added into the preparation of the solid dispersion composition administered orally to improve the flowability and other physical properties. The pharmaceutical excipient can be selected from the group consisting of lactose, starch, sodium carboxymethyl starch, polyvinylpyrrolidone, cross-linked carboxymethyl cellulose sodium, maltose dextrin, crystalline cellulose, calcium phosphate, the mixture of calcium bicarbonate and crystalline cellulose. Furthermore, lubricants such as stearic acid, magnesium stearate and talc may be added.

BRIEF DESCRIPTION OF THE DRAWINGS

The objects and characteristics of the present invention can be illustrated by the following drawings. In the drawings.

EXAMPLES

Figure 1:
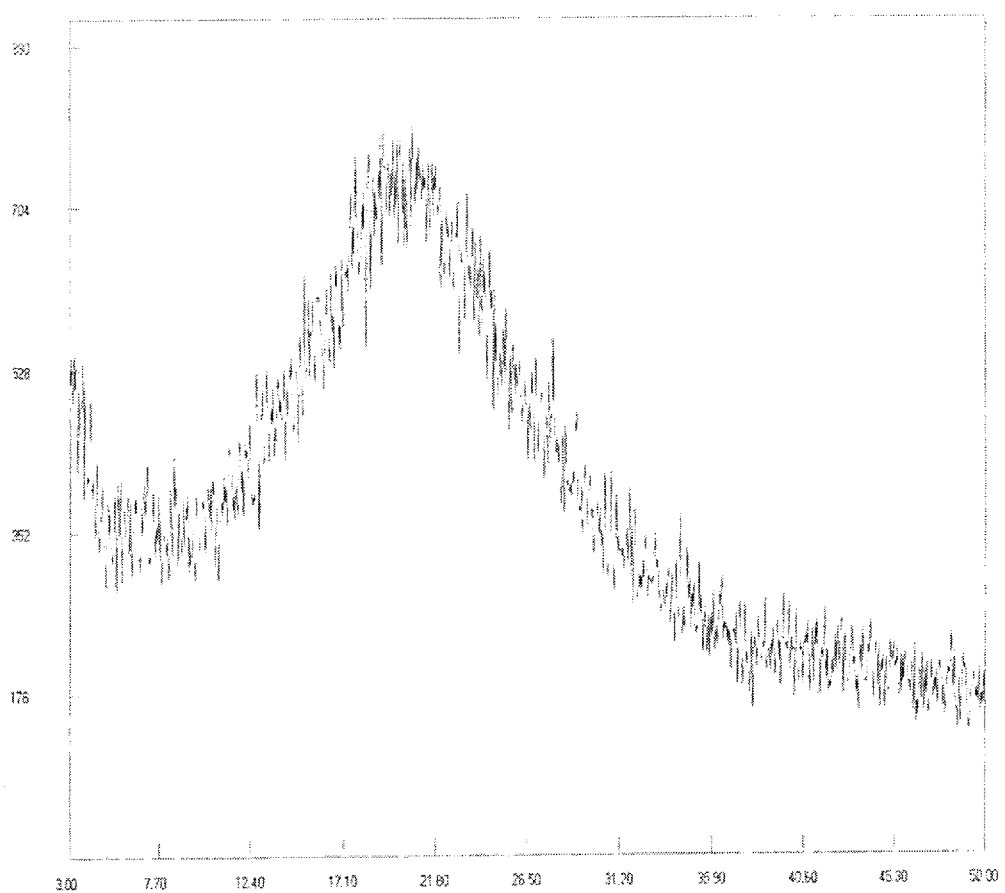
FIG. 1 shows the X-ray powder diffraction pattern of the solid dispersion in Example 1.
Figure 2:
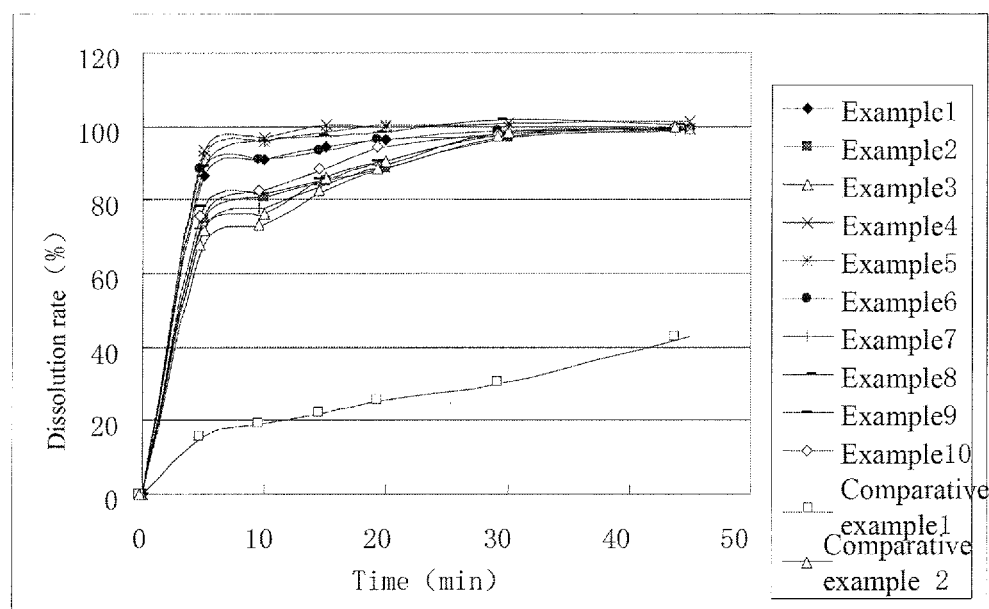
FIG. 2 shows the in vitro release profiles of the solid dispersions in Examples 1-10 and Comparative examples 1 and 2.
Figure 3:
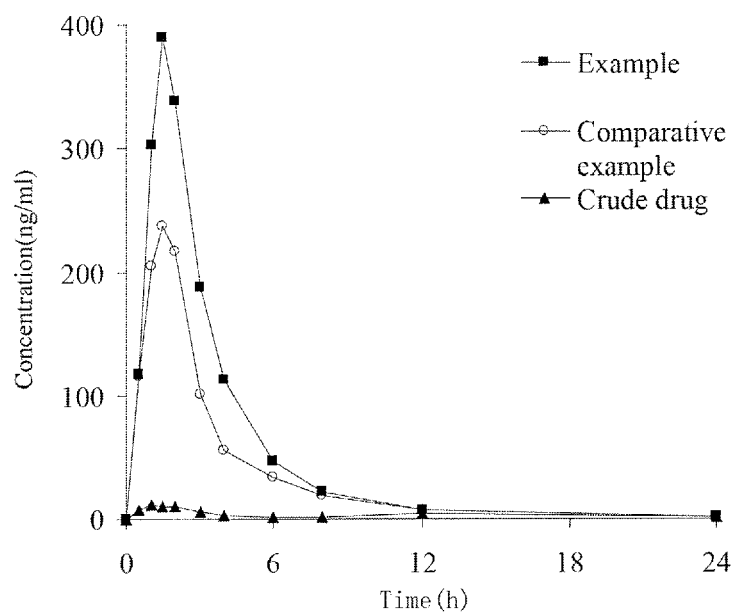
FIG. 3 shows the in vivo bioavailability profiles of raw material, and the solid dispersions in Example 4 and Comparative example 2.

The present invention is more specifically described by the following examples, however, the present invention is not limited to those examples in any way.

Example 1

20 g tolvaptan were added to the mixture of dichloromethane and ethanol, and stirred until the solution was clear. 10 g cross-linked polyvinylpyrrolidone were added to ethanol and dispersed well. The solution of tolvaptan and the dispersion of cross-linked polyvinylpyrrolidone were mixed and spray-dried to give the tolvaptan solid dispersion which has a particle size distribution of 1 μm~400 μm and an average particle diameter of 52 μm.

Example 2

20 g tolvaptan were added to the mixture of dichloromethane and ethanol, and stirred until the solution was clear. 2 g cross-linked polyvinylpyrrolidone were added to ethanol and dispersed well. The solution of tolvaptan and the dispersion of cross-linked polyvinylpyrrolidone were mixed and spray-dried to give the tolvaptan solid dispersion which has a particle size distribution of 1 μm~400 μm and an average particle diameter of 52 μm.

Example 3

20 g tolvaptan were added to the mixture of dichloromethane and ethanol, and stirred until the solution was clear. 200 g cross-linked polyvinylpyrrolidone were added to ethanol and dispersed well. The solution of tolvaptan and the dispersion of cross-linked polyvinylpyrrolidone were mixed and spray-dried to give the tolvaptan solid dispersion which has a particle size distribution of 1 μm~400 μm and an average particle diameter of 52 μm.

Example 4

20 g tolvaptan were added to the mixture of dichloromethane and ethanol and stirred until the solution was clear. 1 g polyvinylpyrrolidone was added to the mixture of dichloromethane and ethanol and stirred until the solution was clear. 10 g cross-linked polyvinylpyrrolidone were added to the mixture of dichloromethane and ethanol and dispersed well. The solution of tolvaptan and the dispersion of other ingredients were mixed and spray-dried to give the tolvaptan solid dispersion which has a particle size distribution of 1 μm~100 μm and an average particle diameter of 25 μm.

Example 5

20 g tolvaptan were added to the mixture of dichloromethane and ethanol and stirred until the solution was clear. 1 g hydroxypropylmethyl cellulose was added to the mixture of dichloromethane and ethanol and stirred until the solution was clear. 10 g cross-linked polyvinylpyrrolidone were added to the mixture of dichloromethane and ethanol and dispersed well. The solution of tolvaptan and the dispersion of other ingredients were mixed and spray-dried to give the tolvaptan solid dispersion which had a particle size distribution of 1 μm~100 μm and an average particle diameter of 25 μm.

Example 6

20 g tolvaptan were added to the mixture of dichloromethane and ethanol and stirred until the solution was clear. 1 g hydroxyethyl cellulose was added to the mixture of dichloromethane and ethanol and stirred until the solution was clear. 10 g cross-linked polyvinylpyrrolidone were added to the mixture of dichloromethane and ethanol and dispersed well. The solution of tolvaptan and the dispersion of other ingredients were mixed and spray-dried to give the tolvaptan solid dispersion which has a particle size distribution of 1 μm~100 μm and an average particle diameter of 25 μm.

Example 7

20 g tolvaptan were added to the mixture of dichloromethane and ethanol and stirred until the solution was clear. 1 g sodium carboxymethyl cellulose was added to the mixture of dichloromethane and ethanol and stirred until the solution was clear. 10 g cross-linked polyvinylpyrrolidone were added to the mixture of dichloromethane and ethanol and dispersed well. The solution of tolvaptan and the dispersion of other ingredients were mixed and spray-dried to give the tolvaptan solid dispersion which had a particle size distribution of 1 μm~100 μm and an average particle diameter of 25 μm.

Example 8

20 g tolvaptan were added to the mixture of dichloromethane and ethanol and stirred until the solution was clear. 1 g methylcellulose was added to the mixture of dichloromethane and ethanol and stirred until the solution was clear. 10 g cross-linked polyvinylpyrrolidone were added to the mixture of dichloromethane and ethanol and dispersed well. The solution of tolvaptan and the dispersion of other ingredients were mixed and spray-dried to give the tolvaptan solid dispersion which has a particle size distribution of 1 μm~100 μm and an average particle diameter of 25 μm.

Example 9

20 g tolvaptan were added to the mixture of dichloromethane and ethanol and stirred until the solution was clear. 2 g sucrose ester was added to the mixture of dichloromethane and ethanol and stirred until the solution was clear. 10 g cross-linked polyvinylpyrrolidone were added to the mixture of dichloromethane and ethanol and dispersed well. The solution of tolvaptan and the dispersion of other ingredients were mixed and spray-dried to give the tolvaptan solid dispersion which has a particle size distribution of 1 μm~100 μm and an average particle diameter of 25 μm.

Example 10

20 g tolvaptan were added to the mixture of dichloromethane and ethanol and stirred until the solution was clear. 0.5 g polyvinyl alcohol was added to the mixture of dichloromethane and ethanol and stirred until the solution was clear. 10 g cross-linked polyvinylpyrrolidone were added to the mixture of dichloromethane and ethanol and dispersed well. The solution of tolvaptan and the dispersion of other ingredients were mixed and spray-dried to give the tolvaptan solid dispersion which has a particle size distribution of 1 μm~100 μm and an average particle diameter of 25 μm.

Comparative Example 1

10 g tolvaptan were added to the mixture of dichloromethane and ethanol and stirred until the solution was clear. The solution was spray-dried directly to give the tolvaptan amorphous powder which has a particle diameter distribution of 0.01 μm~200 μm and an average particle diameter of 28 μm.

Comparative Example 2

20 g tolvaptan were added to the mixture of dichloromethane and ethanol and stirred until the solution was clear. Then 10 g hydroxypropyl cellulose were added to the solution and dispersed well. The mixture was spray-dried to give the tolvaptan solid dispersion which has a particle diameter distribution of 1 μm~400 μm and an average particle diameter of 56 μm.

Dissolution Test

Q.S. (the amount is equal to 100 mg of tolvaptan) of the powder prepared in Examples 1-10, Comparative examples and the control (crystal material with a particle diameter distribution of 1400 μm and an average diameter of 83 μm) were added to the dissolution tester. 0.2% w/v sodium dodecylsulfate aqueous solution was used as the solvent. The dissolution test was performed using the paddle blade method with the rotation speed of 100 rpm. A sample was taken at 5 min, 10 min, 15 min, 20 min, 30 min, and 45 min to determine the absorbance and calculate the dissolution rate.

The determination of the dissolution rate (%) is as follows: dissolve a certain amount of tolvaptan in methanol; transfer 5 ml of the solution to a 100-ml volumetric flask and then dilute with 0.2% (w/v) sodium dodecylsulfate aqueous solution to give a 20 μg/ml standard solution; the absorbance of the standard solution and the sample solution was determined at wavelengths of 269 nm and 330 nm. The dissolution rate can be obtained by the ratio of the difference of the absorbance of standard solution and the control and the difference of the absorbance of the sample solution and control. The results are shown in the following Table 1.

TABLE 1

| (min) | Time | | | | | |
|---|---|---|---|---|---|---|
| | 5 | 10 | 15 | 20 | 30 | 45 |
| Example 1 | 86.5% | 90.9% | 94.2% | 96.3% | 97.6% | 99.2% |
| Example 2 | 74.7% | 80.6% | 85.2% | 88.5% | 97.1% | 98.7% |
| Example 3 | 71.6% | 76.0% | 86.0% | 90.5% | 98.2% | 99.1% |
| Example 4 | 93.4% | 96.8% | 100.2% | 99.6% | 100.9% | 101.4% |
| Example 5 | 92.0% | 95.9% | 98.3% | 100.4% | 99.9% | 99.1% |
| Example 6 | 88.5% | 90.8% | 93.4% | 96.5% | 98.7% | 99.2% |
| Example 7 | 72.5% | 77.7% | 84.3% | 89.5% | 98.2% | 98.7% |
| Example 8 | 89.2% | 95.8% | 97.2% | 98.6% | 101.9% | 100.1% |
| Example 9 | 78.1% | 81.6% | 85.8% | 90.7% | 98.0% | 99.5% |
| Example 10 | 75.7% | 82.6% | 88.4% | 94.2% | 97.8% | 100.0% |
| Comparative example 1 | 15.9% | 19.1% | 22.2% | 25.8% | 30.7% | 42.8% |
| Comparative example 2 | 68.1% | 73.5% | 82.4% | 88.7% | 97.4% | 99.8% |

The results show that:

(i) The release characteristic is improved significantly by using cross-linked polyvinylpyrrolidone as the carrier of the tolvaptan solid dispersion, compared to the solid dispersion known in the art using hydroxypropyl cellulose as the carrier. The ratio of the drug and the cross-linked polyvinylpyrrolidone by weight can be selected in a large range, the ratio in the range of 1:0.1-10 is preferable and the ratio in the range of 1:0.5 is most preferable.

(ii) Other water-soluble polymers can be used simultaneously as a carrier in combination with cross-linked polyvinylpyrrolidone on the basis of using cross-linked polyvinylpyrrolidone as the carrier of tolvaptan solid dispersion. Comparative study discovered that, because the water-soluble polymers can further improve the properties of the solid dispersion, there is no particular limitation on the amount of the water-soluble polymers to be added. When the ratio of the water-soluble polymer and cross-linked polyvinylpyrrolidone reaches 1:5-20, it shows a significant improvement effect statistically, more preferably 1:10. Among all the water-soluble polymers, hydroxyethyl cellulose and methylcellulose are preferable, and hydroxypropyl cellulose and polyvinylpyrrolidone are most preferable.

Example 11

| The solid dispersion prepared in Example 1 | 18 g |
|---|---|
| Lactose | 24 g |
| Maize starch | 6 g |
| Macrocrystalline cellulose | 6 g |
| 5% hydroxypropyl cellulose solution | q.s. |
| Cross-linked polyvinylpyrrolidone | 3 g |
| Magnesium stearate | 0.3 g |

The solid dispersion was sieved through a 40-mesh sieve, the excipients were sieved through a 80-mesh sieve. The solid dispersion and the excipients were mixed well. 5% hydroxypropyl cellulose solution was used to granulate, and then dried by aeration-drying at 50° C. The dry-granules were sieved through a 20-mesh sieve. Cross-linked polyvinylpyrrolidone and magnesium stearate were added and mixed well. The mixture was put into capsules.

Example 12

| The solid dispersion prepared in Example 3 | 58 g |
|---|---|
| Lactose | 15 g |
| Microcrystalline cellulose | 5 g |
| 5% hydroxypropyl cellulose solution | q.s. |
| Cross-linked carmellose | 3 g |
| Magnesium stearate | 0.3 g |
| Opadry | 1.8 g |

The solid dispersion was sieved through a 40-mesh sieve and the excipients were sieved through an 80-mesh sieve. The solid dispersion and the excipients were mixed well. 5% hydroxypropyl cellulose solution was used to granulate, and then dried by aeration-drying at 50° C. The dry-granules were sieved through a 20-mesh sieve. Cross-linked carmellose and magnesium stearate were added and mixed well. The mixture was made into tablets and coated.

Example 13

| The solid dispersion prepared in Example 2 | 95 g |
|---|---|
| Lactose | 10 g |
| Pregelatinized starch | 2 g |
| Microcrystalline cellulose | 2 g |
| 5% polyvinylpyrrolidone solution | q.s. |
| Low substituted hydroxypropylcellulose | 5 g |
| Magnesium stearate | 0.3 g |

The solid dispersion was sieved through a 40-mesh sieve, the excipients were sieved through a 80-mesh sieve. The solid dispersion and the excipients were mixed well. 5% polyvinylpyrrolidone solution was used to granulate, and then dried by aeration-drying at 50° C. The dry-granules were sieved through a 20-mesh sieve. Low substituted hydroxypropyl cellulose and magnesium stearate were added and mixed well. The mixture was made into tablets.

What is claimed:

1. A pharmaceutical amorphous solid dispersion, comprising amorphous tolvaptan or a salt thereof as an active ingredient, a carrier comprising cross-linked polyvinylpyrrolidone, and one or more water soluble polymers, wherein the one or more water soluble polymers are selected from the group consisting of polyvinylpyrrolidone, hydroxypropylmethyl cellulose, hydroxyethylcellulose and methylcellulose, wherein the amorphous tolvaptan or salt thereof, the cross-linked polyvinylpyrrolidone, and the one or more water soluble polymers are at a ratio of 2:1:0.1 by weight.

2. The pharmaceutical amorphous solid dispersion according to claim 1, wherein the solid dispersion consists of the active ingredient, the cross-linked polyvinylpyrrolidone and the one or more water soluble polymers.

3. The pharmaceutical amorphous solid dispersion according to claim 1, wherein the one or more water soluble polymers are hydroxypropylmethyl cellulose or polyvinylpyrrolidone.

4. A preparation method of the pharmaceutical amorphous solid dispersion according to claim 1, comprising:
  i) dissolving tolvaptan or a salt thereof in a first organic solvent to obtain a first solution;
  ii) dissolving or dispersing the cross-linked polyvinylpyrrolidone and one or more water soluble polymers in a second organic solvent to obtain a second solution, or separately dissolving or dispersing the cross-linked polyvinylpyrrolidone and the one or more water soluble polymers in a second solvent and one or more additional organic solvents to obtain a second solution and one or more additional solutions, respectively,
  wherein each of the first, second and additional organic solvents independently, optionally contains water depending on the need of the dissolving or the dispersing;
  iii) mixing the solutions obtained in steps i) and ii), and
  iv) removing the first, second and additional organic solvents, to obtain the solid dispersion mixture.

5. The preparation method according to claim 4, wherein the step of removing the organic solvents comprises evaporation, a spray drying method, or a fluidized bed drying method.

6. The preparation method according to claim 4, wherein at least one of the first, second and additional organic solvents is selected from the group consisting of methanol, ethanol, isopropanol, acetone, butanone, dichloromethane, dichloroethane, trichloromethane, and carbon tetrachloride.

7. The method according to claim 6, wherein at least one of the first, second and additional organic solvents is a mixture of ethanol and dichloromethane; or each of the second and additional organic solvents is ethanol.

8. A pharmaceutical composition comprising the amorphous solid dispersion according to claim 1.

* * * * *